US012521332B2

(12) United States Patent
Liu et al.

(10) Patent No.: US 12,521,332 B2
(45) Date of Patent: Jan. 13, 2026

(54) HAIR CARE COMPOSITION

(71) Applicant: Conopco, Inc., Englewood Cliffs, NJ (US)

(72) Inventors: Jian Liu, Shanghai (CN); Yingying Pi, Shanghai (CN)

(73) Assignee: Conopco, Inc., Hoboken, NJ (US)

( * ) Notice: Subject to any disclaimer, the term of this patent is extended or adjusted under 35 U.S.C. 154(b) by 840 days.

(21) Appl. No.: 17/777,721

(22) PCT Filed: Oct. 27, 2020

(86) PCT No.: PCT/EP2020/080111
§ 371 (c)(1),
(2) Date: May 18, 2022

(87) PCT Pub. No.: WO2021/099073
PCT Pub. Date: May 27, 2021

(65) Prior Publication Data

US 2022/0409506 A1 Dec. 29, 2022

(30) Foreign Application Priority Data

Nov. 19, 2019 (WO) ................ PCT/CN2019/119553
Dec. 17, 2019 (EP) .................................... 19216800

(51) Int. Cl.

| | |
|---|---|
| ***A61K 8/42*** | (2006.01) |
| ***A61K 8/46*** | (2006.01) |
| ***A61K 8/49*** | (2006.01) |
| ***A61K 8/73*** | (2006.01) |
| ***A61Q 5/00*** | (2006.01) |
| ***A61Q 5/02*** | (2006.01) |

(52) U.S. Cl.
CPC ................ *A61K 8/42* (2013.01); *A61K 8/463* (2013.01); *A61K 8/4926* (2013.01); *A61K 8/737* (2013.01); *A61Q 5/006* (2013.01); *A61Q 5/02* (2013.01)

(58) Field of Classification Search
CPC ............. A61K 8/42; A61Q 5/006; A61Q 5/02
See application file for complete search history.

(56) References Cited

U.S. PATENT DOCUMENTS

| | | | |
|---|---|---|---|
| 3,958,581 | A | 5/1976 | Abegg et al. |
| 3,962,418 | A | 6/1976 | Birkofer |
| 5,234,618 | A | 8/1993 | Kamegai et al. |
| 5,858,342 | A | 1/1999 | Camerley et al. |
| 9,949,909 | B2 | 4/2018 | Klug et al. |
| 10,172,774 | B2 | 1/2019 | Klug et al. |
| 2008/0167284 | A1 | 7/2008 | Bhogal et al. |
| 2013/0150338 | A1 | 6/2013 | Ananthapadmanabhan et al. |
| 2014/0242018 | A1 | 8/2014 | Zasloff |
| 2015/0126616 | A1 | 5/2015 | Klug et al. |
| 2015/0150767 | A1 | 6/2015 | Klug et al. |
| 2016/0272666 | A1 | 9/2016 | Klug et al. |
| 2016/0324743 | A1 | 11/2016 | Orr et al. |
| 2016/0361243 | A1 | 12/2016 | Klug et al. |
| 2017/0000710 | A1 | 1/2017 | Klug et al. |
| 2019/0076344 | A1 | 3/2019 | Klug et al. |
| 2019/0117544 | A1 | 4/2019 | Zhao et al. |
| 2019/0307668 | A1* | 10/2019 | Stricane .................. A61K 8/44 |
| 2019/0365619 | A1 | 12/2019 | Ceballos et al. |
| 2019/0374794 | A1 | 12/2019 | Kamps et al. |

FOREIGN PATENT DOCUMENTS

| | | |
|---|---|---|
| CN | 1120851 | 4/1996 |
| CN | 1177372 | 3/1998 |
| CN | 103052427 | 4/2013 |
| CN | 103068445 | 4/2013 |
| CN | 110312504 | 10/2019 |
| DE | 202013011412 | 3/2014 |
| DE | 202013011413 | 3/2014 |
| RU | 227612 | 3/2006 |
| RU | 2385719 | 4/2010 |
| WO | WO9205764 | 4/1992 |
| WO | WO9418292 | 8/1994 |
| WO | WO9517880 | 7/1995 |
| WO | WO9631188 | 10/1996 |
| WO | WO2004004677 | 1/2004 |
| WO | WO2012022552 | 2/2012 |
| WO | WO2013178697 | 12/2013 |
| WO | WO2013178701 | 12/2013 |
| WO | WO2014123916 | 8/2014 |

(Continued)

OTHER PUBLICATIONS

Search Report and Written Opinion in PCT/EP2020/080111; Jan. 19, 2021; World Intellectual Property Org. (WIPO).

(Continued)

*Primary Examiner* — Andrew S Rosenthal
(74) *Attorney, Agent, or Firm* — Stephanie S. DelPonte

(57) ABSTRACT

A hair care composition is disclosed comprising a polyhydroxy fatty acid amide surfactant of general formula (I): wherein $R^1$ is a $C_1$-$C_4$alkyl groups or hydroxy-substituted $C_1$-$C_4$ alkyl groups; $R^2CO$ is a linear or branched, saturated or unsaturated $C_3$-$C_{10}$ acyl group, preferably $C_8$-$C_{10}$ acyl group, an ethoxylated alkyl sulfate anionic surfactant having a formula $R^3O(CH_2CH_2O)nSO_3M$, wherein $R^3$ is an alkyl or alkenyl having from 8 to 18 carbon atoms; M is a solubilising cation comprising sodium, potassium, ammonium, substituted ammonium or mixtures thereof; n is the degree of ethoxylation of from 0.5 to 3, and from 0.01 to 10% by weight of an anti-dandruff agent selected from piroctone olamine, azole based anti-fungal agents and mixtures thereof, wherein the weight ratio of the ethoxylated alkyl sulfate anionic surfactant to the polyhydroxy fatty acid amide surfactant ranges from 1:10 to 10:1.

(I)

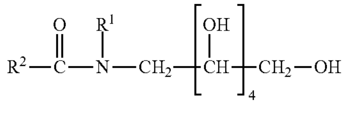

15 Claims, No Drawings

(56) References Cited

FOREIGN PATENT DOCUMENTS

| | | |
|---|---|---|
| WO | WO2014206555 | 12/2014 |
| WO | WO2015074750 | 5/2015 |
| WO | WO2015078586 | 6/2015 |
| WO | WO2015078587 | 6/2015 |
| WO | WO2016058836 | 4/2016 |
| WO | WO2016058837 | 4/2016 |
| WO | WO2016062619 | 4/2016 |
| WO | WO2016174256 | 11/2016 |
| WO | WO2016179503 | 11/2016 |
| WO | WO2017216162 | 12/2017 |
| WO | WO2018095813 | 5/2018 |
| WO | WO2018154298 | 8/2018 |

OTHER PUBLICATIONS

Search Report and Written Opinion in EP19216800.3; May 12, 2020; European Patent Office (EPO).
Written Opinion in PCT/EP2020/080111; Oct. 29, 2021; World Intellectual Property Org. (WIPO).
International Preliminary Report on Patentability in PCT/EP2020/080111; Feb. 7, 2022; World Intellectual Property Org. (WIPO).
Search Report and Written Opinion in PCT/EP2020/080110; Nov. 30, 2020; World Intellectual Property Org. (WIPO).
Written Opinion in PCT/EP2020/080110; Oct. 28, 2021; World Intellectual Property Org. (WIPO).
International Preliminary Report on Patentability in PCT/EP2020/080110.; Nov. 30, 2022; World Intellectual Property Org. (WIPO).
Search Report and Written Opinion in EP19216803.7; May 12, 2020; European Patent Office (EPO).
Orsavova, J., et al., "Fatty Acids Composition of Vegetable Oils and Its Contribution to Dietary Energy Intake and Dependence of Cardiovascular Mortality on Dietary Intake of Fatty Acids", International Journal of Molecular Sciences, 16(2), pp. 12871-12890 (2015).
Colt 45 Soft Texture Hair Wax, Record ID: 6254717; Mintel GNPD; 2 pages (2019).
Supersonik Water-Based Pomade, Record ID: 5646047; Mintel GNPD; 2 pages (2018).
"Discover and new Sensory Dimension in Hair Care Glucotain", Clariant, 8 pages, retrieved from URL: https://www.clariant.com/de/Solutions/Products/2014/11/05/10/01/GlucoTain-Clear (retreived 2020).
"Product Fact Sheet—Glucotain Clear", Clariant, 2 pages, retrieved from the Internet: www.clariant.com/de/Solutions/Products/2014/11/05/10/01/GlucoTain-Clear (retreived 2020).
Co-pending U.S. Appl. No. 17/777,715, filed May 18, 2022.
Sutyagin V.M. et al. "Chemistry and physics of polymers Manual"; Ministry of Education of the Russian Federation; Tomsk Polytechnic University; Editorial House TPU Tomsk; p. 142; 2003.

* cited by examiner

HAIR CARE COMPOSITION

CROSS REFERENCE TO RELATED APPLICATIONS

The present application is a U.S. National Phase Application under 35 U.S.C. § 371 of International Application No. PCT/EP2020/080111 filed Oct. 27, 2020, which claims the benefit of priority to International Application No. PCT/CN2019/119553 filed Nov. 19, 2019, and European Patent Application No. 19216800.3 filed Dec. 17, 2019, the contents of each of which are incorporated by reference herein in their entireties.

TECHNICAL FIELD OF THE INVENTION

This invention relates to hair care compositions comprising a specific mild surfactant and anti-dandruff agents that provide enhanced deposition of anti-dandruff agents onto hair and/or scalp of an individual.

BACKGROUND OF THE INVENTION

Hair care compositions generally provide cleansing or conditioning benefits or a combination of the two. Such compositions typically comprise one or more cleansing surfactants which generally aid in cleaning the hair and the scalp free of undesirable soil, particles and fatty matter. However, preferred hair care composition will provide more benefits than simple cleansing and conditioning. For example, it is desirable to incorporate mild surfactants in hair care compositions so that the hair care compositions are non-irritating and gentle to the scalp.

It is also desirable to incorporate various benefit agents in hair care composition to provide benefits in addition to cleansing and conditioning. For example, anti-dandruff benefit has been provided through hair care compositions. Dandruff is an issue that affects many people globally. The condition is manifested by the shedding of clumps of dead skin cells from the scalp. These are white in colour and provide an aesthetically displeasing appearance. A factor that contributes to dandruff is certain members of the *Malassezia* yeasts. To combat these, anti-dandruff products have included certain anti-dandruff agents which have anti-fungal activity, for example, piroctone olamine (Octopirox®), azole based anti-fungal agents (e.g. climbazole, ketoconazole), selenium sulfide or combinations thereof. Many anti-dandruff hair care compositions, however, do not provide sufficient anti-dandruff agent deposition during the excessive rinsing process. The anti-dandruff agents are simply rinsed away and therefore provide little or no anti-dandruff benefit. Therefore, it is always desired to efficiently deposit anti-dandruff agents onto hair and/or scalp to provide good anti-dandruff performance.

WO 2015/078587 A1 discloses compositions containing at least one N-alkyl-N-acylglucamine as component A, dimethiconol as component B, at least one anionic surfactant as component C, optionally at least one betaine surfactant as component D, optionally at least one further surfactant as component E, water as component F, and optionally at least one further additive as component G, which compositions can be used as hair-washing agents.

WO 2013/178697 A2 discloses N-methyl-N-acylglucamines are suitable as thickening agents in aqueous surfactant solutions containing one or more anionic surfactants of the group including alkyl ether sulfates and alkyl sulfates, the N-methyl-N-acylglucamines containing at least 60 wt % of N-methyl-N-acylglucamines that have a $C_{12}$, $C_{14}$-acyl group or an unsaturated $C_{18}$-acyl group and at the same time less than 5 wt % of N-methyl-N-acylglucamines that contain an acyl group $<C_{12}$.

WO 9205764 A1 discloses the mixed conditioning/anti-dandruff shampoo composition containing 3.6 wt % of coconut N-methyl glucose amide, 1.5 wt % of dimethicone and 1.5 wt % selenium sulfide.

US 2019365619 A1 discloses an antidandruff cleansing composition salicylic acid and a surfactant system.

U.S. Pat. No. 5,234,618 A discloses a detergent composition comprising (a) 0.1 to 95% by weight of a saccharide nonionic surfactant and (b) 0.01 to 5% by weight of an antibacterial agent.

There is continuing need for a hair care composition which provides desirable mildness and improved deposition of anti-dandruff agents.

SUMMARY OF THE INVENTION

In a first aspect, the present invention is directed to a hair care composition comprising:

(a) a polyhydroxy fatty acid amide surfactant of general formula (I):

(I)

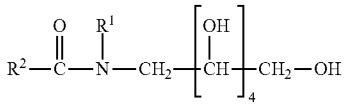

wherein $R^1$ is a $C_1$-$C_4$ alkyl groups or hydroxy-substituted $C_1$-$C_4$ alkyl groups; $R^2CO$ is a linear or branched, saturated or unsaturated $C_3$-$C_{10}$ acyl group, preferably $C_6$-$C_{10}$ acyl group;

(b) an ethoxylated alkyl sulfate anionic surfactant having a formula $R^3O\ (CH_2CH_2O)_nSO_3M$, wherein $R^3$ is an alkyl or alkenyl having from 8 to 18 carbon atoms; M is a solubilising cation comprising sodium, potassium, ammonium, substituted ammonium or mixtures thereof; n is the degree of ethoxylation of from 0.5 to 3; and (c) from 0.01 to 10% by weight of an anti-dandruff agent selected from piroctone olamine, azole based anti-fungal agents and mixtures thereof;

wherein the weight ratio of the ethoxylated alkyl sulfate anionic surfactant to the polyhydroxy fatty acid amide surfactant ranges from 1:10 to 10:1.

In a second aspect, the present invention is directed to a packaged hair care product comprising the hair care composition of the first aspect of this invention.

In a third aspect, the present invention is directed to a method of depositing anti-dandruff agents onto scalp comprising the step of applying the hair care composition of any embodiment of the first aspect of this invention onto scalp surfaces of an individual followed by rinsing the surfaces with water.

All other aspects of the present invention will more readily become apparent upon considering the detailed description and examples which follow.

DETAILED DESCRIPTION

Except in the examples, or where otherwise explicitly indicated, all numbers in this description indicating amounts of material or conditions of reaction, physical properties of materials and/or use may optionally be understood as modified by the word "about".

All amounts are by weight of the final hair care composition, unless otherwise specified. It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

"Hair care composition", as used herein, is meant to include a composition for topical application to hair and/or scalp of mammals, especially humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, or bar. Non-limiting examples of such compositions include leave-on hair lotions, creams, and rinse-off shampoos, conditioners, shower gels, or toilet bar. The composition of the present invention is preferably a rinse-off composition, especially preferred being a shampoo or a conditioner and most preferably a shampoo.

The polyhydroxy fatty acid amide surfactant suitable for use in compositions of the present invention is a non-ionic surfactant represented by the general formula (I):

(I)

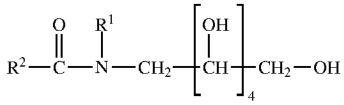

wherein $R^1$ is a $C_1$-$C_4$ alkyl groups or hydroxy-substituted $C_1$-$C_4$ alkyl groups; $R^2CO$ is a linear or branched, saturated or unsaturated $C_3$-$C_{10}$ acyl group, preferably $C_6$-$C_{10}$ acyl group. More preferably, $R^1$ is a methyl group, the acyl group $R^2CO$ is derived from caproic acid, caprylic acid or capric acid.

Suitable examples of the polyhydroxy fatty acid amide that may be used in this invention include capryloyl methyl glucamide, caproyl methyl glucamide or mixtures thereof. In a preferred embodiment, the polyhydroxy fatty acid amide comprises at least 60% by weight of a mixture of capryloyl methyl glucamide and caproyl methyl glucamide based on total weight of the polyhydroxy fatty acid amide, preferably from 65% to 100% by weight of a mixture of capryloyl methyl glucamide and caproyl methyl glucamide, more preferably from 70 to 100%, based on total weight of the polyhydroxy fatty acid amide. In another preferred embodiment, the polyhydroxy fatty acid amide is a mixture of capryloyl methyl glucamide and caproyl methyl glucamide.

The polyhydroxy fatty acid amide preferably comprises the capryloyl methyl glucamide and the caproyl methyl glucamide in a weight ratio ranging from 1:5 to 5:1, more preferably from 1:2 to 3:1.

The composition of the present invention may additionally have small fractions of polyhydroxy fatty acid amide derived from long chain fatty acids, in particular those which comprise $C_{12}$-, $C_{14}$-, $C_{16}$-, $C_{18}$-acyl groups.

An example of a suitable polyhydroxy fatty acid amide is commercially available from Clariant International Ltd under the trade name GLUCOTAIN® CLEAR.

Typically, the hair care composition comprises the polyhydroxy fatty acid amide in an amount of from 0.1 to 45%, more preferably from 1 to 30% and most preferably from 5 to 20%, based on total weight of the hair care composition and including all ranges subsumed therein.

The hair care composition of the present invention also comprises an ethoxylated anionic surfactant which is an ethoxylated alkyl sulfate anionic surfactant having a formula $R^3O(CH_2CH_2O)_nSO_3M$, wherein $R^3$ is an alkyl or alkenyl group having from 8 to 18 (preferably 12 to 18) carbon atoms, M is a solubilising cation comprising sodium, potassium, ammonium, substituted ammonium or mixtures thereof, n is the degree of ethoxylation of from 0.5 to 3, preferably from 1 to 3. An example is sodium lauryl ether sulfate (SLES).

"Degree of Ethoxylation", as used herein, refers to the average number of moles of ethylene oxide unit per mole of ethoxylated product. The degree of ethoxylation is measured using $^1H$ NMR in a solvent of deuterium oxide ($D_2O$). For example, the degree of ethoxylation of sodium lauryl ether sulfate (SLES) is measured using $^1H$ NMR (Bruker-Biospin, 400 MHz) and the spectrum is recorded at 25° C. The sample for measurement using NMR is prepared as follows: the sample is dispersed in $D_2O$ in a centrifugal tube and sonicated, then the solution is filtered and transferred to an NMR tube. The peaks corresponding to the protons of the sample appear at about 3.98 ppm, about 4.15 ppm and between about 3.58 to about 3.84 ppm. The peaks corresponding to the protons for —$CH_2$—, which appear at about 4.15 ppm and about 3.98 ppm, are integrated as A1. The peaks corresponding to the four protons for —$OCH_2CH_2$—, which appear at 4.15 ppm and between about 3.58 to about 3.84 ppm, are also integrated as A2. The degree of ethoxylation of SLES may be calculated as follows:

$$\text{The degree of ethoxylation} = \frac{(A2/4)}{(A1/2)}$$

Preferred ethoxylated alkyl sulfate anionic surfactant is sodium lauryl ether sulfate (SLES) having a degree of ethoxylation of from 0.5 to 3, preferably from 1 to 3.

The ethoxylated alkyl sulfate anionic surfactant is typically present in an amount of from 0.1 to 45%, more preferably from 1 to 30% and most preferably from 5 to 20%, based on total weight of the hair care composition and including all ranges subsumed therein.

The hair care composition comprises the ethoxylated alkyl sulfate anionic surfactant and the polyhydroxy fatty acid amide surfactant in a weight ratio of from 1:10 to 10:1, preferably from 1:6 to 6:1 and more preferably from 1:4 to 4:1.

The hair care composition comprises anti-dandruff agents, which are compounds that are active against dandruff and are typically anti-microbial agents and preferably anti-fungal agents. Suitable anti-dandruff agents that may be used in this invention are selected from piroctone olamine (Octopirox®), azole based anti-fungal agents and mixtures thereof.

Without wishing to be bound by theory the present inventors believe that surfactant system of this invention works for piroctone olamine or azole based anti-fungal agents (especially climbazole) because both of them can be stabilized and solved in micelles, and the deposition can be improved by reducing the agent's solubility in the system.

The preferred azole based anti-fungal agent is ketoconazole, climbazole or mixtures thereof. Preferably, the anti-dandruff agent is selected from piroctone olamine, climbazole and mixtures thereof. In an especially preferred embodiment, the anti-dandruff agent is piroctone olamine.

Typically, the hair care composition of the invention comprises the anti-dandruff agent in an amount of from 0.01 to 10%, more preferably from 0.01 to 5%, more preferably still from 0.05 to 2%, and most preferably from 0.05 to 1.5%, based on total weight of the hair care composition and including all ranges subsumed therein.

The pH of the hair care composition is preferably equal to or higher than 4.0, more preferably in the range of 4.0 to 7.0.

In addition to the polyhydroxy fatty acid amide and the ethoxylated alkyl sulfate anionic surfactant, it is preferred if the hair care composition also comprises other surfactants.

Examples of suitable anionic surfactants include alkyl sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule. Typical examples of anionic surfactants include, but not limited to, sodium oleyl succinate, ammonium lauryl sulphosuccinate, sodium lauryl sulphate, sodium lauryl ether sulphosuccinate, ammonium lauryl sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate. Mixtures of any of the foregoing anionic surfactants may also be suitable. Generally, the total amount of additional anionic surfactant in hair care composition of the present invention ranges from 0.5 to 45%, more preferably from 1.5 to 35% and most preferably from 5 to 20%, based on the total weight of the hair care composition and including all ranges subsumed therein.

The hair care composition may also comprise other non-ionic surfactants in addition to the polyhydroxy fatty acid amide, which can be included in an amount of from 0.1 to 10%, preferably from 0.5 to 8%, more preferably from 1 to 5%, based on total weight of the hair care composition and including all ranges subsumed therein. Examples of suitable non-ionic surfactants include condensation products of aliphatic ($C_8$-$C_{18}$) primary or secondary linear or branched chain alcohols or phenols with alkylene oxides, usually ethylene oxide and generally having from 6 to 30 ethylene oxide groups. Alkyl ethoxylates are preferred, more preferably are alkyl ethoxylates having the formula $R^4$—$(OCH_2CH_2)_mOH$, where $R^4$ is an alkyl chain having from 12 to 15 carbon atoms and m is from 5 to 9.

Other suitable non-ionic surfactants include mono- or di-alkyl alkanolamides. Examples include coco mono- or di-ethanolamide and coco mono-isopropanolamide.

Further non-ionic surfactants which can be included in compositions of the invention are the alkyl polyglycosides (APGs). Typically, APG is one which comprises an alkyl group connected (optionally via a bridging group) to a block of one or more glycosyl groups. Preferred APGs are defined by the following formula:

$$R^5O\text{-}(G)_k$$

wherein $R^5$ is a branched or straight chain alkyl group which may be saturated or unsaturated and G is a saccharide group. $R^5$ may represent a mean alkyl chain length of from $C_5$ to $C_{20}$. Preferably $R^5$ represents a mean alkyl chain length of from $C_8$ to $C_{12}$. Most preferably the value of $R^5$ lies between 9.5 and 10.5. G may be selected from $C_5$ or $C_6$ monosaccharide residues and is preferably a glucoside. G may be selected from the group comprising glucose, xylose, lactose, fructose, mannose and derivatives thereof. Preferably G is glucose. The degree of polymerisation, k, may have a value of from 1 to 10 or more; preferably, the value of k lies from 1.1 to 2; most preferably the value of m lies from 1.3 to 1.5. Suitable alkyl polyglycosides for use in the invention are commercially available and include for example those materials identified as: Oramix NS10 ex Seppic; Plantaren 1200 and Plantaren 2000 ex Henkel.

The hair care composition may also comprise amphoteric or zwitterionic surfactants, which can be included in an amount of from 0.1 to 10%, preferably from 0.5 to 8%, more preferably from 1 to 5%, based on total weight of the hair care composition and including all ranges subsumed therein. Examples include alkyl amine oxides, alkyl betaines, alkyl amidopropyl betaines, alkyl sulphobetaines (sultaines), alkyl amphoacetates, alkyl amphopropionates, alkyl amidopropyl hydroxysultaines, wherein the alkyl group has from 8 to 19 carbon atoms. Preferably, the co-surfactant is a betaine surfactant. Typical amphoteric and zwitterionic surfactants for use in the invention include lauryl amine oxide, cocodimethyl sulphopropyl betaine, lauryl betaine, cocamidopropyl betaine and sodium cocoamphoacetate. Cocamidopropyl betaine (CAPB) is particularly preferred.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

The composition may further comprise a cationic polymer. Suitable cationic polymers may be homopolymers or be formed from two or more types of monomers. The molecular weight of the polymer will generally be between 5,000 and 10,000,000 g/mol, typically at least 10,000 g/mol and preferably from 100,000 to 2,000,000 g/mol.

The polymers will have cationic nitrogen containing groups such as quaternary ammonium or protonated amino groups, or a mixture thereof. The cationic nitrogen containing group will generally be present as a substituent on a fraction of the total monomer units of the cationic polymer. Thus when the polymer is not a homopolymer it can contain spacer non-cationic monomer units. The ratio of the cationic to non-cationic monomer units is selected to give a polymer having a cationic charge density in the required range.

Suitable cationic polymers include, for example, copolymers of vinyl monomers having cationic amine or quaternary ammonium functionalities with water soluble spacer monomers such as (meth)acrylamide, alkyl and dialkyl (meth) acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol and ethylene glycol.

Preferably, the cationic polymer is a cationic polysaccharide polymer such as cationic cellulose derivatives, cationic starch derivatives, and cationic guar gum derivatives. Suitably, such cationic polysaccharide polymers have a molecular weight of from 100,000 g/mol to 2,300,000 g/mol, more preferably from 150,000 g/mol to 2,000,000 g/mol. Such cationic polysaccharide polymers preferably have a cationic charge density from 0.1 to 4 meq/g.

Cationic polysaccharide polymers suitable for use in compositions of this invention include those represented by the general formula:

$$A\text{-}O\text{—}[R^6\text{—}N^+(R^7)(R^8)(R^9)X^-]$$

wherein: A is an anhydroglucose residual group, such as a starch or cellulose anhydroglucose residual. $R^6$ is an alkylene, oxyalkylene, polyoxyalkylene, or hydroxyalkylene group, or combination thereof. $R^7$, $R^8$ and $R^9$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^7$, $R^8$ and $R^9$) is preferably about 20 or less, and X is an anionic counterion.

Cationic cellulose is available from Amerchol Corp. (Edison, NJ, USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, NJ, USA) under the tradename Polymer LM-200.

Other suitable cationic polysaccharide polymers include quaternary nitrogen-containing cellulose ethers (e.g. as described in U.S. Pat. No. 3,962,418) and copolymers of etherified cellulose and starch (e.g. as described in U.S. Pat. No. 3,958,581).

A particularly preferred type of cationic polysaccharide polymer that can be used in compositions of the present invention is a cationic guar gum derivative, such as guar hydroxypropyltrimonium chloride (for example, commercially available from Solvay in their Jaguar trademark series or from Ashland in their N-Hance trademark series). Examples of such materials are Jaguar® C-13S, Jaguar® C-14S, Jaguar® C-17, Jaguar® Excel, Jaguar® C-162, Jaguar® C-500, Jaguar® Optima, Jaguar® LS, N-Hance™ BF17, N-Hance™ BF13 and N-Hance™ CCG45.

Mixtures of any of the above cationic polymers may be used. The cationic polymer preferably comprises cationic cellulose derivatives, cationic guar gum derivatives or mixtures thereof. Guar hydroxypropyltrimonium chloride is particularly preferred.

When used, the cationic polymer will generally be present in the hair care composition of the present invention in an amount of from 0.001 to 1% by weight of the hair care composition, more preferably from 0.01 to 0.5%, and most preferably from 0.03 to 0.3%, based on total weight of the hair care composition and including all ranges subsumed therein.

The hair care composition may additionally comprise a conditioning agent to provide conditioning benefit. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. Preferably, the conditioning agent is non-volatile, meaning that it has a vapour pressure of less than 1000 Pa at 25° C. and one atmospheric pressure.

Preferably, the hair care composition comprises discrete dispersed droplets of a water-insoluble conditioning agent, which has a mean droplet diameter ($D_{3,2}$) of less than 15 microns, preferably less than 10 microns, more preferably less than 5 microns, most preferably less than 3 microns. The mean droplet diameter ($D_{3,2}$) of a water-insoluble conditioning agent may be measured by means of a laser light scattering technique, for example using a 2600D Particle Sizer from Malvern Instruments.

The water-insoluble conditioning agent may include non-silicone conditioning agent comprising non-silicone oily or fatty materials such as hydrocarbon oils, fatty esters and mixtures thereof. Preferably, the water-insoluble conditioning agent is emulsified silicone oil.

Suitable silicones include polydiorganosiloxanes, in particular polydimethylsiloxanes which have the CTFA designation dimethicone. Also suitable for use in compositions of this invention (particularly shampoos and conditioners) are polydimethyl siloxanes having hydroxyl end groups, which have the CTFA designation dimethiconol. Also suitable for use in compositions of this invention are silicone gums having a slight degree of cross-linking, as are described for example in WO 96/31188. Preferably, the silicone oil comprises dimethicone, dimethiconol or a mixture thereof.

Suitable emulsified silicones for use in the hair care compositions of this invention are available as pre-formed silicone emulsions from suppliers of silicones such as Dow Silicones Corporation and GE silicones. The use of such pre-formed silicone emulsion is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Examples of suitable pre-formed silicone emulsions include MEM-7128, MEM-1785, MEM-1788, all available from Dow Silicones Corporation. These are emulsions of dimethiconol/dimethicone.

Another class of silicones which may be used are functionalized silicones such as amino functional silicones, meaning a silicone containing at least one primary, secondary or tertiary amine group, or a quaternary ammonium group. Examples of suitable amino functional silicones include polysiloxanes having the CTFA designation "amodimethicone."

The water-insoluble conditioning agent is generally present in hair care composition of this invention in an amount from 0.05 to 15%, preferably from 0.1 to 10%, more preferably from 0.5 to 8%, most preferably from 1 to 5%, based on total weight of the hair care composition and including all ranges subsumed therein.

Preferably the composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

The suspending agent is generally present in hair care composition of this invention in an amount of from 0.1 to 10%, more preferably from 0.5 to 6%, and most preferably from 0.5 to 4%, based on total weight of the hair care composition and including all ranges subsumed therein.

The hair care composition is preferably aqueous, i.e. they have water or an aqueous solution or a lyotropic liquid crystalline phase as their major component. The composition typically will comprise water from 50 to 98%, more preferably from 60 to 90%, based on total weight of the hair care composition.

Preservatives may also be incorporated into the hair care composition of this invention to protect against the growth of potentially harmful microorganisms. Suitable traditional preservatives include alkyl esters of parahydroxybenzoic acid, hydantoin derivatives, propionate salts, and a variety of quaternary ammonium compounds. Illustrative yet non-limiting examples of the types of preservatives that may be used in this invention include, for examples, phenoxyethanol, sodium salicylate, methyl paraben, butyl paraben, propyl paraben, diazolidinyl urea, sodium dehydroacetate, benzyl alcohol, sodium benzoate, iodopropynyl butylcarbamate, caprylyl glycol, disodium EDTA or mixtures thereof. In an especially preferred embodiment, the preservative is phenoxyethanol, sodium salicylate or a mixture thereof. Preservatives are preferably employed in amounts ranging from 0.01 to 2% by weight of the hair care composition.

The hair care composition of the present invention may contain other ingredients which are common in the art to enhance physical properties and performances. Suitable ingredients include but are not limited to fragrance, dyes and pigments, pH adjusting agents, pearlescers or opacifiers, viscosity modifiers, thickeners, and natural hair nutrients such as botanicals, fruit extracts, sugar derivatives and amino acids. Such ingredients typically and collectively make up less than 20% by weight of the composition, and preferably, from 0.0 to 15% by weight, and most preferably, from 0.01 to 12% by weight of the composition, including all ranges subsumed therein.

The compositions of the invention are primarily intended for topical application to scalp and/or at least a portion of the hair of an individual, either in rinse-off or leave-on compositions, preferably in rinse-off compositions like shampoos.

The following examples are provided to facilitate an understanding of the present invention. The examples are not provided to limit the scope of the claims.

EXAMPLES

Example 1

This example demonstrates the improved deposition of anti-dandruff agents by using a combination of polyhydroxy fatty amide surfactant and ethoxylated alkyl sulfate anionic surfactant. Compositions were prepared according to the formulations detailed in Table 1. All ingredients are expressed by weight percent of the total formulation, and as level of active ingredient.

TABLE 1

| Ingredient | Samples 1 | 2 |
|---|---|---|
| Sodium lauryl ether sulfatse (1EO) | 13.00 | — |
| Piroctone olamine | 0.50 | 0.50 |
| Disodium EDTA | 0.05 | 0.05 |
| Sodium benzoate | 0.50 | 0.50 |
| Carbopol 980 | 0.35 | 0.35 |
| Guar Hydroxypropyltrimonium chloride[a] | 0.20 | 0.20 |
| Dimethiconol[b] | 0.78 | 0.78 |
| Dimethicone[c] | 0.52 | 0.52 |
| Capryloyl/caproyl methyl glucamide[d] | — | 13.00 |
| Perfume | 0.80 | 0.80 |
| Sodium chloride | 1.00 | 1.00 |
| Water | To 100 | To 100 |

[a]Commercial guar hydroxypropyltrimonium chloride has a weight average molecular weight of from 1.0 to 1.5 million g/mol and a degree of substitution of from 0.16 to 0.20 sourced from Lamberti.
[b]Commercial dimethiconol which has a particle size of 0.2 μm from Dow Silicones Corporation.
[c]Commercial dimethicone which has a particle size of 10 μm from Dow Silicones Corporation.
[d]Commercially available capryloyl/caproyl methyl glucamide under the trade name Glucotain ® Clear from Clariant.

TABLE 2

| Ingredient | Samples 3 | 4 | 5 | 6 | 7 | 8 |
|---|---|---|---|---|---|---|
| Sodium lauryl ether sulfate (1EO) | 13.00 | 11.00 | 9.00 | 5.00 | 4.00 | 2.00 |
| Piroctone olamine | 0.50 | 0.50 | 0.50 | 0.50 | 0.50 | 0.50 |
| Disodium EDTA | 0.05 | 0.05 | 0.05 | 0.05 | 0.05 | 0.05 |
| Sodium benzoate | 0.50 | 0.50 | 0.50 | 0.50 | 0.50 | 0.50 |
| Carbopol 980 | 0.35 | 0.35 | 0.35 | 0.35 | 0.35 | 0.35 |
| Guar Hydroxypropyl-trimonium chloride[a] | 0.20 | 0.20 | 0.20 | 0.20 | 0.20 | 0.20 |
| Dimethiconol[b] | 0.78 | 0.78 | 0.78 | 0.78 | 0.78 | 0.78 |
| Dimethicone[c] | 0.52 | 0.52 | 0.52 | 0.52 | 0.52 | 0.52 |
| Capryloyl/caproyl methyl glucamide[d] | — | 2.00 | 4.00 | 8.00 | 9.00 | 11.00 |
| Perfume | 0.80 | 0.80 | 0.80 | 0.80 | 0.80 | 0.80 |
| Sodium chloride | 1.00 | 1.00 | 1.00 | 1.00 | 1.00 | 1.00 |
| Water | To 100 | To 100 | To 100 | To 100 | To 100 | To 100 |

Methods

Citric acid was added to the samples to adjust the pH to 4.3. About 0.2 grams of the test sample was taken on artificial skin (VITRO-SKIN from IMS testing group). This was diluted with 1.8 mL water and rubbed with a plastic rod for 30 seconds. The artificial skin surface was then rinsed twice with water, first time with 4 mL water for 30 second and then again with 4 mL water for 30 seconds. The deposition of piroctone olamine on the skin (10.75 $cm^2$ per plate) was measured using HPLC method.

Results

The average deposition (of five such experiments) are reported in Table 3 and Table 4 (error represents standard deviation for duplicate measurements).

TABLE3

| Samples | 1 | 2 |
|---|---|---|
| Piroctone olamine deposition (μg/plate) | 8.94 ± 1.85 | 9.74 ± 1.22 |

TABLE 4

| Samples | 3 | 4 | 5 | 6 | 7 | 8 |
|---|---|---|---|---|---|---|
| Piroctone olamine deposition (μg/plate) | 8.03 ± 1.04 | 9.92 ± 0.93 | 13.00 ± 1.91 | 14.35 ± 1.03 | 18.60 ± 0.76 | 16.10 ± 1.02 |

The data in table 3 indicates that sample 1 comprising sodium lauryl ether sulfate provided comparable deposition of piroctone olamine to sample 2 comprising polyhydroxy fatty acid amide.

Table 4 further indicates that samples 4 to 8 comprising a combination of sodium lauryl ether sulfate and polyhydroxy fatty acid amide provided significantly better ($p<0.05$) deposition of piroctone olamine than sample 3 comprising only sodium lauryl ether sulfate (used as control).

The invention claimed is:

1. A hair care composition comprising:

from 5% to 11% by weight of a polyhydroxy fatty acid amide surfactant selected from capryloyl methyl glucamide, caproyl methyl glucamide, or any mixture thereof;

from 2% to 9% by weight of an ethoxylated alkyl sulfate anionic surfactant wherein the ethoxylated alkyl sulfate anionic surfactant is sodium lauryl ether sulfate; and from 0.05 to 0.5 wt % by weight of piroctone olamine, wherein the weight ratio of the ethoxylated alkyl sulfate anionic surfactant to the polyhydroxy fatty acid amide surfactant ranges from 1:6 to 6:1.

2. The hair care composition according to claim 1, wherein the polyhydroxy fatty acid amide comprises capryloyl methyl glucamide and caproyl methyl glucamide in a weight ratio ranging from 1:5 to 5:1.

3. The hair care composition according to claim 1, wherein the composition further comprises a cationic polymer.

4. The hair care composition according to claim 3, wherein the cationic polymer comprises cationic cellulose derivatives, cationic guar gum derivatives, or mixtures thereof.

5. The hair care composition according to claim 1, wherein the composition is a shampoo.

6. The hair care composition according to claim 1, wherein the composition comprises the ethoxylated alkyl sulfate anionic surfactant and the polyhydroxy fatty acid amide surfactant in a weight ratio of from 1:4 to 4:1.

7. The hair care composition of claim 1 further comprising a cationic polymer, wherein the cationic polymer comprises guar hydroxypropyltrimonium chloride.

8. The hair care composition of claim 7, wherein the composition comprises from 0.03% to 0.3% by weight of the cationic polymer.

9. The hair care composition of claim 1 further comprising a silicone oil.

10. The hair care composition of claim 9, wherein the silicone oil comprises dimethicone, dimethiconol or a mixture thereof.

11. The hair care composition of claim 1 further comprising at least one of alkyl sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, alkyl ether carboxylic acids or any sodium, magnesium, ammonium and mono, di-and triethanolamine salts thereof.

12. The hair care composition of claim 1 further comprising at least one alkyl polyglycoside.

13. The hair care composition of claim 1 further comprising at least one amphoteric surfactant, zwitterionic surfactant, or a combination thereof.

14. The hair care composition of claim 1 further comprising at least one conditioning agent.

15. A method of depositing anti-dandruff agents onto scalp comprising the step of applying the hair care composition according to claim 1 onto scalp surfaces of an individual followed by rinsing the surfaces with water.

* * * * *